United States Patent
Tour et al.

(10) Patent No.: US 11,246,962 B2
(45) Date of Patent: Feb. 15, 2022

(54) NEURONAL SCAFFOLD-WATER SOLUBLE GRAPHENE FOR TREATMENT OF SEVERED SPINAL CORDS AND NEURONAL REPAIR

(71) Applicant: WILLIAM MARSH RICE UNIVERSITY, Houston, TX (US)

(72) Inventors: James M. Tour, Bellaire, TX (US); William Sikkema, Langley (CA)

(73) Assignee: William Marsh Rice University, Houston, TX (US)

(*) Notice: Subject to any disclaimer, the term of this patent is extended or adjusted under 35 U.S.C. 154(b) by 0 days.

(21) Appl. No.: 16/327,675

(22) PCT Filed: Aug. 22, 2017

(86) PCT No.: PCT/US2017/047955
§ 371 (c)(1),
(2) Date: Feb. 22, 2019

(87) PCT Pub. No.: WO2018/039194
PCT Pub. Date: Mar. 1, 2018

(65) Prior Publication Data
US 2019/0184063 A1    Jun. 20, 2019

Related U.S. Application Data

(60) Provisional application No. 62/377,947, filed on Aug. 22, 2016.

(51) Int. Cl.
C08L 71/02 (2006.01)
A61L 27/44 (2006.01)
A61L 27/52 (2006.01)

(52) U.S. Cl.
CPC .............. *A61L 27/443* (2013.01); *A61L 27/52* (2013.01); *C08L 71/02* (2013.01); *A61L 2400/12* (2013.01); *A61L 2400/18* (2013.01); *A61L 2420/04* (2013.01); *A61L 2420/08* (2013.01); *A61L 2430/32* (2013.01)

(58) Field of Classification Search
CPC ........ A61L 27/443; A61L 27/40; A61L 27/44; A61L 27/52; C08L 71/02
USPC ....................................................... 523/113
See application file for complete search history.

(56) References Cited

U.S. PATENT DOCUMENTS

| | | | |
|---|---|---|---|
| 8,808,580 B2* | 8/2014 | Plee .......... | C08L 53/02 252/510 |
| 9,233,166 B2* | 1/2016 | Dai ............ | A61K 47/6929 |
| 9,460,827 B2* | 10/2016 | Khe .......... | H01B 1/24 |

(Continued)

OTHER PUBLICATIONS

Officer Kamila Miklos; International Search Report and Written Opinion; PCT/US2017/047955; dated Nov. 8, 2017; 12 pages.

(Continued)

*Primary Examiner* — Jane L Stanley
(74) *Attorney, Agent, or Firm* — Dickinson Wright PLLC; Ross Spencer Garsson

(57) ABSTRACT

Graphene compositions used for neuronal repair and treatments, and, in particular neuronal scaffold-water soluble graphene for treatment of severed spinal cords and other neuronal repairs. The neuronal scaffold-water soluble graphene can be PEGylated GNR used in combination with a fusogen agent, such as PEG600.

18 Claims, 14 Drawing Sheets

(56) References Cited

U.S. PATENT DOCUMENTS

| | | | |
|---|---|---|---|
| 2010/0028681 A1* | 2/2010 | Dai | B82Y 40/00 |
| | | | 428/408 |
| 2013/0230496 A1 | 9/2013 | Mohapatra et al. | |
| 2014/0048748 A1* | 2/2014 | Tour | B82Y 30/00 |
| | | | 252/511 |
| 2015/0099214 A1* | 4/2015 | Khe | H01B 1/04 |
| | | | 429/523 |
| 2018/0028715 A1* | 2/2018 | Eisenfrats | A61K 9/0024 |
| 2018/0147296 A1* | 5/2018 | Sitharaman | A61P 35/00 |

OTHER PUBLICATIONS

Officer Yukari Nakamura; International Preliminary Report on Patentability; PCT/US2017/047955; dated Mar. 7, 2019; 5 pages.

* cited by examiner

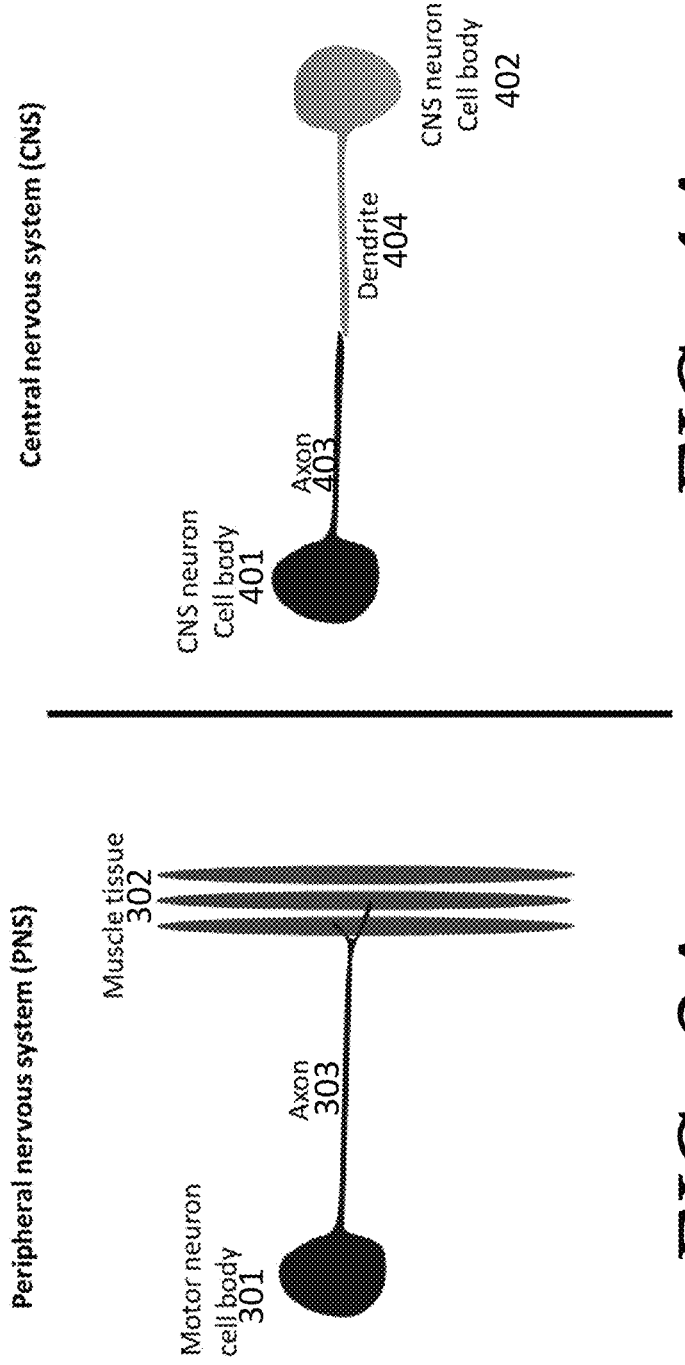

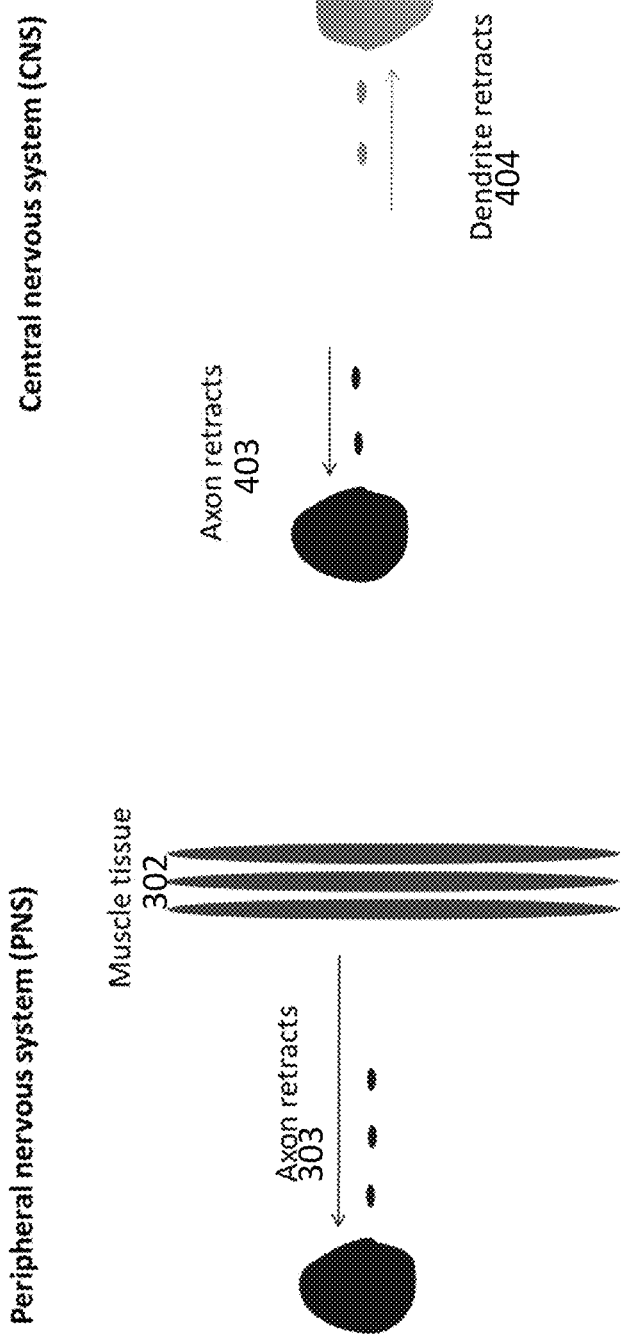

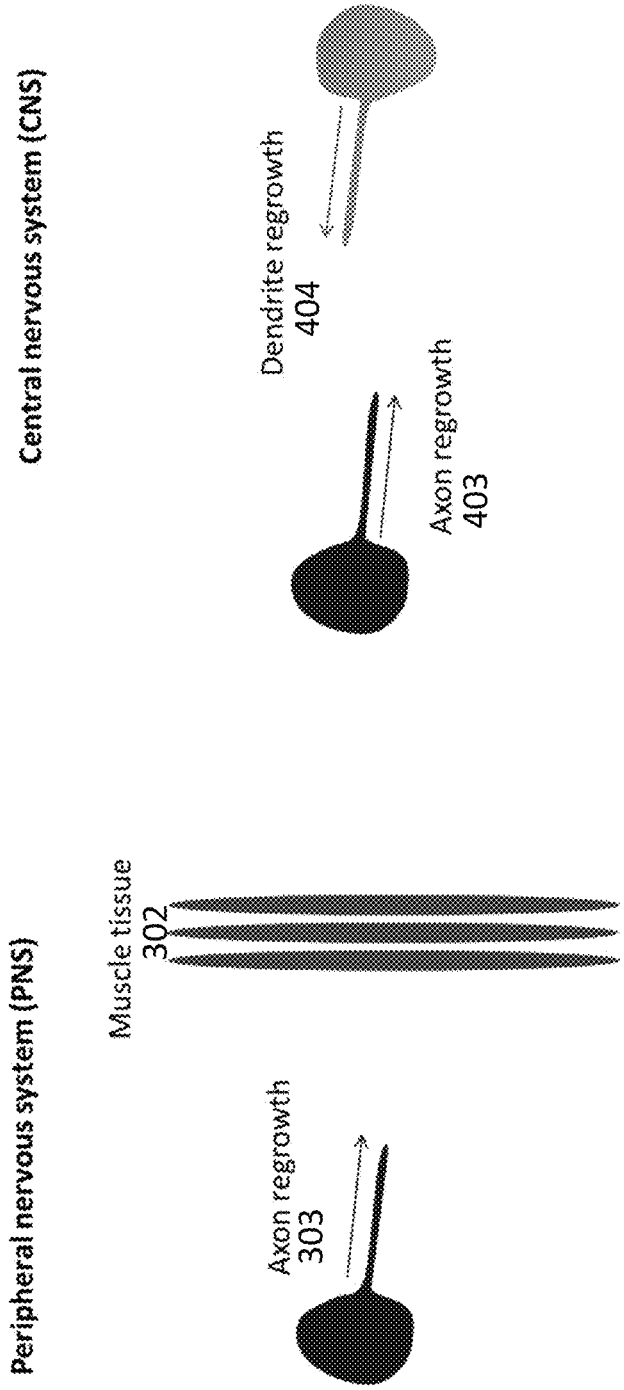

NEURONAL SCAFFOLD-WATER SOLUBLE GRAPHENE FOR TREATMENT OF SEVERED SPINAL CORDS AND NEURONAL REPAIR

CROSS-REFERENCE TO RELATED PATENT APPLICATIONS

This application is a 35 U.S.C § 371 national application of PCT Application No. PCT/US17/47955, filed on Aug. 22, 2017, entitled "Neuronal Scaffold-Water Soluble Graphene For Treatment Of Severed Spinal Cords And Neuronal Repair", which claims priority to U.S. Patent Appl. Ser. No. 62/377,947, filed Aug. 22, 2016, entitled "Neuronal Scaffold-Water Soluble Graphene For Fast Repair of Severed Spinal Cords," and which patent applications are commonly owned by the owner of the present invention. These patent applications are hereby incorporated by reference in their entirety for all purposes.

FIELD OF INVENTION

The present invention relates to graphene compositions used for neuronal repair and treatments, and, in particular neuronal scaffold-water soluble graphene for treatment of severed spinal cords and other neuronal repairs.

BACKGROUND OF INVENTION

Spinal cord injuries cost the American public 0.2% of the GDP and yet almost all people affected have little to no recovery. Of the quarter-million US citizens with spinal cord injury (SCI) and spinal cord disorders, 8% are military personnel that receive compensation due to the cause or nature of their injury. The symptoms of SCI on people are wide ranging from tetraplegia to neuropathic pain and lower body systems dysfunction, including digestive problems and sexual dysfunction. In addition, many people with SCI present depression related to chronic pain and/or disability. There are several types of SCI, but two main categories: one-third of the cases are complete SCI and two-thirds of the cases are incomplete SCI. Notably, less than 1% persons hospitalized for SCI experience recovery by the time of their hospital discharge. The US annual costs of SCIs are $37 billion per year, not to mention the lost productivity of the injured and the caregivers.

Few options are available for the treatment of SCI, despite years of research on the subject. Supportive medical care and early surgical decompression, when applicable, remain the cornerstones of management following acute injury. SCI can also be divided into primary and secondary injury. Primary SCI refers to the initial insult to the spinal cord. It includes a heterogeneous group of mechanisms such as contusion/compression, stretch injury, and transection of various degrees. These injuries can lead to axonal disruption and tissue degeneration.

A consequence of SCI is the formation of scar tissue and posttraumatic microcystic myelomalacia. The extent of each of these post-injury maladies depends on injury severity. Two types of scar tissue can be formed, namely, glial and fibrous. The glial scar consists of a loose network of astrocytic processes connected by tight junctions. There has recently been a challenge to a prevailing dogma that glial scars are regarded as a failure of axonal regrowth in the central nervous system. Instead, astrocytes in SCI lesions were found to express multiple axon-growth-supporting molecules responsible for stimulating axonal regrowth past scar-forming astrocytes. Fibrous scarring is made up of extracellular matrix deposition and type IV collagen, which form a tight barrier. In addition to creating a mechanical barrier, both types of scars may obstruct neuronal regeneration. Current tissue engineering research is focused on constructing a permissive environment at the site of injury that would support axonal regeneration.

Development of a bioscaffold that assists with neural tissue regeneration and the prevention/bypass of scar formation is an ongoing area of research. Graphene, a two-dimensional (2D) sheet of $sp^2$-hybridized graphitic carbon, is a substance of recent interest in neurosurgery, one of the applications of which is as a SCI bioscaffold because the following unique properties give graphene tremendous biomedical potential: Zero-gap semiconductor characteristics, high thermal conductivity, high surface area-to-volume ratio, and chemical modifiability, which allows for functionalization of biotherapeutic molecules. Most studies on graphene have focused on novel uses in electrical transport and composite materials, with little focus on biological applications, excluding nascent investigations in biosensing. Thus, the bioapplicability and potential cytotoxic effects of graphene have only recently been studied. Two recent noteworthy studies have examined the cytotoxic effects of graphene and graphene oxide (GO) in solution on pheochromocytoma-derived PC12 cells. Solubilized graphene, however, does not mimic the needs for growth surfaces.

Two-dimensional graphene films have been used for studying neuronal growth in vitro, however, they do not translate well to in vivo applications.

Accordingly, a need remains for water-soluble materials that can be used as neuronal scaffolds for treatment of severed spinal cords and other neuronal repairs.

SUMMARY OF INVENTION

The present invention relates to

In general, in one embodiment, the invention features a composition that includes functionalized graphene nanoribbons and a fusogen agent. The functionalized graphene nanoribbons include water solubilizing addends functionalized at the edges of the graphene nanoribbons. The functionalized graphene nanoribbons are mixed with the fusogen agent.

Implementations of the invention can include one or more of the following features:

The functionalized graphene nanoribbons can be water soluble.

The functionalized graphene nanoribbons can be mixed into a solution of the fusogen agent. The functionalized graphene nanoribbons in the composition can be in an amount between about 0.1 wt % and about 5 wt %.

The amount of the functionalized graphene nanoribbons in the composition can be between about 0.5 wt % and about 1 wt %.

The fusogen agent can be hydrophilic. The functionalized graphene nanoribbons can be soluble or dispersible in the fusogen agent.

The composition can be operable for use in a use selected from a group consisting of spinal cord repairs, spinal cord treatments, neuronal repairs, neuronal treatments, brain tissue repairs, brain tissue treatments, and whole-body transplants.

The addends can include PEG.

The addends can be selected from a group consisting of PEG, ethylene oxide, propylene oxide, vinyl acetate, vinyl monomers, water soluble electrophiles, polypropylene glycol, polyethylene imine (PEI), PEG-PEI block copolymers, polyvinyl pyrrolidone (PVP), polyvinyl alcohol (PVA), polyacrylic acid, dextrose, starch, pectin, agarose, polysaccharides, 2-aminoethanesulfonic acid, and combinations thereof.

The fusogen agent can be hydrophilic. The functionalized graphene nanoribbons can be soluble or dispersible in the fusogen agent.

The fusogen agent can include PEG having an average molecular weight greater than 500.

The fusogen agent can include PEG600.

The fusogen agent can be selected from a group consisting of PEG, poly(vinyl alcohol), poly(acrylic acid), poly(hydroxyalkyl acrylates), poly(hydroxalkyl methacrylates), and combinations thereof.

The functionalized graphene nanoribbons can be soluble or dispersible in the fusogen agent.

The functionalized graphene nanoribbons can have an electrical conductivity of at least about 0.1 S/cm.

The electrical conductivity can be at least about 1 S/cm.

The electrical conductivity can be at least about 10 S/cm.

The functionalized graphene nanoribbons can have an electrical conductivity that is at least 10% of electrical conductivity of pristine graphene nanoribbons.

The composition can include a graphene nanoribbon hydrogel.

The composition can include functionalized graphene nanoribbons support by a 3D graphene scaffold.

Substantially all of the addends can be functionalized on the edges of the graphene nanoribbons.

At least 90% of the addends can be functionalized on the edges the graphene nanoribbons.

In general, in another embodiment, the invention features a method that includes selecting a composition including functionalized graphene nanoribbons. The functionalized graphene nanoribbons are edge functionalized with water-soluble addends. The method further includes utilizing the composition in a treatment or repair selected from a group consisting of spinal cord repairs, spinal cord treatments, neuronal repairs, neuronal treatments, brain tissue repairs, brain tissue treatments, and whole-body transplant.

Implementations of the invention can include one or more of the following features:

The composition can further include a fusogen agent. The functionalized graphene nanoribbons can be mixed with the fusogen agent.

The composition can be at least one of compositions set forth above.

During the step of utilizing the composition in the treatment or repair, the method can further include applying the composition to substantially align the functionalized graphene nanoribbons.

The step of aligning can include a step of shearing.

The method can further include a step of electrical stimulation to facilitate neuron growth.

The step of electrical stimulation can include applying a voltage to the across the treated or repaired area for a pre-set period of time.

The treatment or repair can include a spinal cord treatment or repair.

The treatment or repair can include the treatment or repair of a complete transection of a spinal cord. The step of utilizing the composition can include coating ends of the spinal cord located at the complete transection with the composition and then holding the ends of the spinal cord in contact with one another.

The step of holding the ends of the spinal cord in contact with one another can include compressing the spinal cord along its axis for at least a pre-set period of time.

The pre-set period of time can be at least one day.

The method can further include shearing the composition to align the functionalized nanoribbons along an axis of the spinal cord.

The step of shearing can include contacting the ends of the spinal cord with one another, slightly re-opening a gap between the ends, re-contacting the ends, and holding the ends of the spinal cord in contact with one another.

The method can further include the step of cutting a portion of the spinal cord at or near the complete transaction to form the ends of the spinal cord located at the complete transaction.

The treatment or repair can include the treatment or repair of a partial transection of a spinal cord. The step of utilizing the composition can include filing in the partial transaction of the spinal cord with the composition.

The step of utilization can include a step of aligning the functionalized nanoribbons along an axis of the spinal cord.

The treatment or repair can include the treatment or repair of a contusion of a spinal cord. The method can include cutting a portion of the spinal cord at or near the contusion to form ends of the spinal cord located at or near the contusion. The step of utilizing the composition can include applying the composition between the ends of the spinal cord.

The composition can be applied by filing in the cut out section.

The method can further include a step of applying electrical stimulation across the cut out section filled with the composition.

The electrical stimulation can facilitate neuron growth across the cut out section.

The composition can include a hydrogel of aligned carbon nanoribbons.

The step of utilizing the composition can include coating the ends of the spinal cord and then holding the ends in contact with one another.

The composition can be utilized in a whole-body transplant.

The foregoing has outlined rather broadly the features and technical advantages of the invention in order that the detailed description of the invention that follows may be better understood. Additional features and advantages of the invention will be described hereinafter that form the subject of the claims of the invention. It should be appreciated by those skilled in the art that the conception and the specific embodiments disclosed may be readily utilized as a basis for modifying or designing other structures for carrying out the same purposes of the invention. It should also be realized by those skilled in the art that such equivalent constructions do not depart from the spirit and scope of the invention as set forth in the appended claims.

It is also to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of the description and should not be regarded as limiting.

BRIEF DESCRIPTION OF THE DRAWINGS

FIGS. 3A-3F illustrate the natural repair of severance of nerves in the peripheral nervous system (PNS) (between the motor neuron cell body of the nerve cell and the muscle tissue)

FIGS. 4A-4F illustrate the natural lack of repair of severance of nerves in the central nervous system (CNS) (between the CNS neuron cell bodies of the nerve cells).

DETAILED DESCRIPTION

Figure 1:
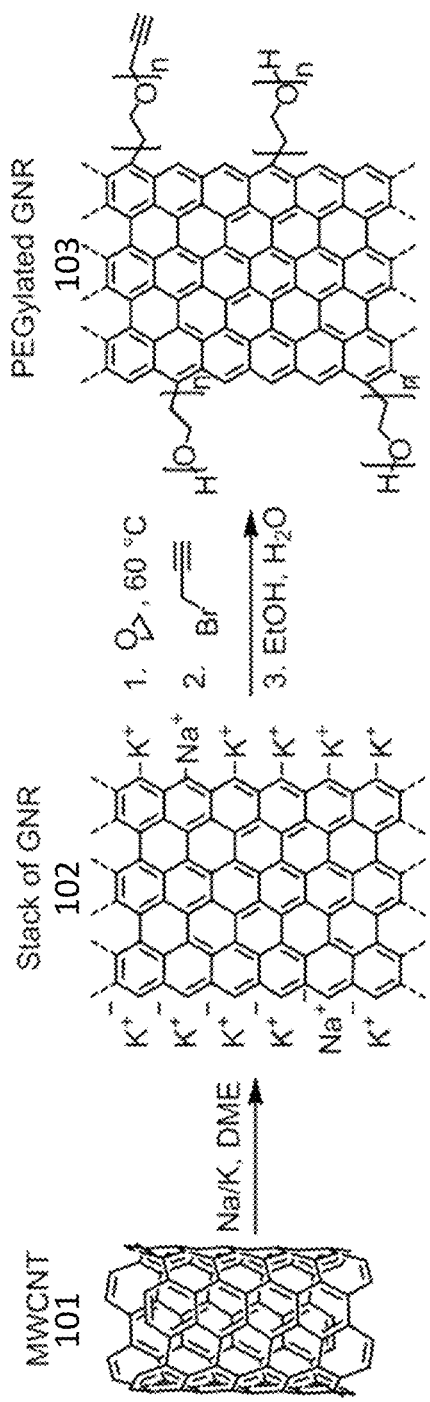
FIG. 1 is a schematic illustrating a chemical process to form PEGylated GNR from multi-wall carbon nanotubes.

In the following description, certain details are set forth such as specific quantities, sizes, etc. so as to provide a thorough understanding of the present embodiments disclosed herein. However, it will be evident to those of ordinary skill in the art that the present disclosure may be practiced without such specific details. In many cases, details concerning such considerations and the like have been omitted inasmuch as such details are not necessary to obtain a complete understanding of the present disclosure and are within the skills of persons of ordinary skill in the relevant art.

Referring to the drawings in general, it will be understood that the illustrations are for the purpose of describing particular embodiments of the disclosure and are not intended to be limiting thereto. Drawings are not necessarily to scale.

While most of the terms used herein will be recognizable to those of ordinary skill in the art, it should be understood, however, that when not explicitly defined, terms should be interpreted as adopting a meaning presently accepted by those of ordinary skill in the art. In cases where the construction of a term would render it meaningless or essentially meaningless, the definition should be taken from Webster's Dictionary, 3rd Edition, 2009. Definitions and/or interpretations should not be incorporated from other patent applications, patents, or publications, related or not, unless specifically stated in this specification or if the incorporation is necessary for maintaining validity.

The following definitions are set forth to aid in understanding of the various embodiments of the present disclosure. Terms in addition to those below are defined, as required, throughout the Detailed Description.

"Graphene nanoribbons" or "GNR" as defined herein, refer to, for example, single- or multiple layers of graphene that have an aspect ratio of greater than about 5 based on their length and their width. As used herein, a material having less than about 50 graphitic carbon layers will be considered to be graphene.

"Functionalized graphene nanoribbons" as defined herein, refer to, for example, graphene nanoribbons that are functionalized at their edges and/or in their basal plane with various moieties (or "addends"), such as organic functional groups, halogens or hydrogen.

"Fusogen agent" or "fusogenic agent" as defined herein, refers to, for example, any chemical, virus, etc. that causes or induces cells, protoplasts, etc., to fuse together.

"Longitudinal opening," as defined herein, refers to, for example, opening of carbon nanotubes substantially parallel to their longitudinal axis to form graphene nanoribbons. As used herein, the term "parallel" refers to an opening of the carbon nanotubes that does not bisect the carbon nanotube's longitudinal axis. In an embodiment, longitudinal opening may involve a relatively straight bond opening process along the sidewall of the carbon nanotube, paralleling but not crossing the longitudinal axis. In another embodiment, longitudinal opening may involve a predominantly spiralwise opening of the carbon nanotubes, again paralleling but not crossing the longitudinal axis.

"Multi-walled carbon nanotubes" or "MWNTs" as used herein will be understood to be inclusive of double-walled carbon nanotubes, triple-walled carbon nanotubes, and any carbon nanotubes having two or more walls.

Water-Soluble Graphene Compositions

The present invention relates to graphene compositions used for neuronal repair and treatments, and, in particular, neuronal scaffold-water soluble graphene for treatment of severed spinal cords and other neuronal repair.

In some embodiments, the present invention pertains to a new composition for neuronal repair (e.g., spinal cord repair, brain tissue repair, treatment of spinal cord injuries, spinal cord fusion, and combinations thereof). In some embodiments, the compositions of the present disclosure include graphene nanoribbons (GNRs) functionalized (e.g., edge-functionalized) with water solubilizing addends (e.g., polyethylene glycol (PEG)). Water solubility or good water dispersibility of the graphene materials, such as GNRs, is important for their use in a 3D system of neurons, and this is conferred by the water solubilizing addends. Also needed is good solubility or dispersibility in hydrophilic polymers, such as PEG.

FIG. 1 is a schematic illustrating a chemical process to form a polyethylene glycol (PEG)-functionalized (PEGylated) graphene nanoribbon (PEG-GNR) 103 from multi-walled carbon nanotubes 101. The multi-wall carbon nanotubes 101 are "unzipped" or "split" to form a stack of GNR 102 and then functionalizing them at their edges with PEG. Typically, the GNRs are predominantly edge functionalized so that the functionalization does not disrupt the basal plane conjugation. In some cases that end of the PEG chain can be capped with a moiety for further functionalization. For example, in the case of PEGylated GNR 103, an alkyne group was added through the addition of propargyl bromide. This alkyne can be used in a subsequent click coupling to append a peptide or other bioactive or bio-recognized moiety.

The compositions of the present disclosure can be fabricated by various steps. For instance, in some embodiments, the MWNTs are first suspended in a mixture of dry 1,2-dimethoxyethane (DME) and a eutectic Na/K alloy. This splits the nanoribbons, and leaves a carbanion decorated nanoribbon. The carbanions are used to macroinitiate the polymerization of oxirane, making water soluble graphene nanoribbons. See Genorio 2012 Further for instance, K is used in the gas phase. See Kosynkin 2011.

Further methods to perform such processes disclosed and taught in (1) Tour PCT '860 Application; (2) Tour PCT '356 Application; (3) with propylene oxide: N. Kim 2016; and (4) with oxirane=ethylene oxide→PEG=PEO GNRs: Lu 2013.

For example, the processes disclosed and taught in were modified to form such PEG-GNR.

In addition to PEG, the water-soluble addends can include ethylene oxide, propylene oxide, vinyl acetate, vinyl monomers, water soluble electrophiles, and combinations thereof. Other suitable polymers for conferring water solubility include, for example, polypropylene glycol, polyethylene imine (PEI), PEG-PEI block copolymers, polyvinyl pyrrolidone (PVP), polyvinyl alcohol (PVA), polyacrylic acid, dextrose, starch, pectin, agarose, and other polysaccharides. Suitable small molecules for conferring water solubility include, for example, 2-aminoethanesulfonic acid.

In some embodiments, the compositions of the present invention include GNRs functionalized with water soluble addends and a neuronal fusogen agent (e.g., a PEG-based fusogen, such as PEG600). In more specific embodiments, the compositions of the present disclosure include water soluble and polyethylene glycol (PEG)-functionalized (PEGylated) graphene nanoribbons (PEG-GNRs) and a neuronal fusogen agent (e.g., PEG600 which is PEG with a weight average molecular weight of 600 grams per mole). Other fusogen agents include other polymers such as poly(vinyl alcohol) or poly(acrylic acid) or poly(hydroxyalkyl acrylates) or poly(hydroxalkyl methacrylates). Other vinyl and step growth polymers could be used as the fusogen host material for dispersing the functionalized GNRs and other vinyl and step growth polymers could be used as the GNR addends predominantly along the GNR edges. Moreover, PEG600 could be substituted by other molecular weight PEG or poly(vinyl alcohol).

In alternative embodiments, surfactant wrapped GNRs can be used.

Moreover, GNRs can be oxidized at the GNR surface to increase the hydrophilicity (but not so much as to excessively mitigate the conductivity The GNR stacks in their native form have a conductivity of about 10 and about 10,000 Siemen/centimeter (S/cm). This level of conductivity is suitable for neuronal growth. If oxidized on the GNR surface, it is preferred to have the conductivity remain greater than about 1 S/cm.

Alternatively, the GNRs can be supported by a 3D graphene scaffold (formed using a 3D printing technique, such as disclosed in Tour PCT '768 Application), which GNR can then by functionalized on their edges.

Further, alternatively, a GNR hydrogel can be utilized in the invention. For example, once could take a standard hydrogel such as chitosan (see, e.g., Leipzig 2011) and infuse it with GNRs to render them conductive and suitable for neuronal reconnection. Further, for example, graphene oxide (GO) hydrogels (see, e.g., Palejwala 2016) that are infused with GNRs can be utilized. Still further, for example, one could make hydrogels form oxidized GNR (see, e.g., Kosynkin 2009 and Sinitskii 2009) and then reduce them to get them conductive, or infuse them with GNRs.

One could also use graphene plates; however, this could lose an advantage of the high aspect ratio of the GNR (i.e. a ratio of 100-200 nm wide for a 5 microns long GNR). Due to this high aspect ratio, much less is needed to get percolation. Using GNR, the present invention is below the percolation threshold at 1 wt %, but not far from it, so as it concentrates when the PEG600 moves out, percolation ensures. If graphene plates are used, then much higher percentages are needed for percolation. The GNRs also have the advantage of being only 100-250 nm wide, so they act as precise tracks for neurons growing from top-down and bottom-up to refuse.

EXAMPLE 1

PEG-GNRs

Multi-walled carbon nanotubes (MWNTs) were obtained from EMD Merck (produced by Mitsui & Co., lot no. 2699-64E) and were used as received. Tetrahydrofuran (THF) was dried over solid KOH for several days, degassed, and freshly distilled from sodium/benzophenone under a $N_2$ atmosphere. All chemicals were purchased from Sigma-Aldrich unless otherwise specified. Thermogravimetric analysis (TGA) measurements were performed on a TA instruments Q-600 Simultaneous TGA/DSC. The temperature was ramped at 10° C./min until 900° C. under argon.

1.0 g of Mitsui MWNTs was added to a 1 L oven-dried, nitrogen-purged, Schlenk flask; 500 mL of THF (alternatively DME could be used) was added. 2.5 mL of eutectic NaK 1:3.3 by mass (1:1.9 by mol) was added under nitrogen. The reaction mixture was stirred at room temperature for 3 days, until very few liquid droplets of NaK remained. The reaction was cooled in a dry ice/acetone bath to −78° C., and 30 g (0.7 mol) of gaseous ethylene oxide was added from a lecture bottle over 90 min. The mixture was slowly brought to room temperature and stirred for 3 days. A mixture of NaH (20 mmol, 0.53 g) and propargyl bromide (20 mmol, 2.4 g) suspended/dissolved in dry toluene was added to terminate the ethylene oxide polymerization. The reaction was quenched by the addition of 20 L of water, and the dark grey precipitate was collected via filtration on a 0.22 µm polyethersulfone (PES) membrane. The dark grey precipitate was filtered through a polytetrafluoroethylene (PTFE) membrane (0.45 µm), followed by crossflow filtration with a 50 kDa MWCO PES filter to remove unbound polymer. The PEG-GNRs final product (1.3 g) was collected on a PTFE membrane (0.45 µm), washed with DI water (3×100 mL), ethanol (3×100 mL), DI water (3×100 mL), and dried under high vacuum overnight. The propargyl units were added to some of the termini for future peptide additions if desired.

Figures 2A, 2B:
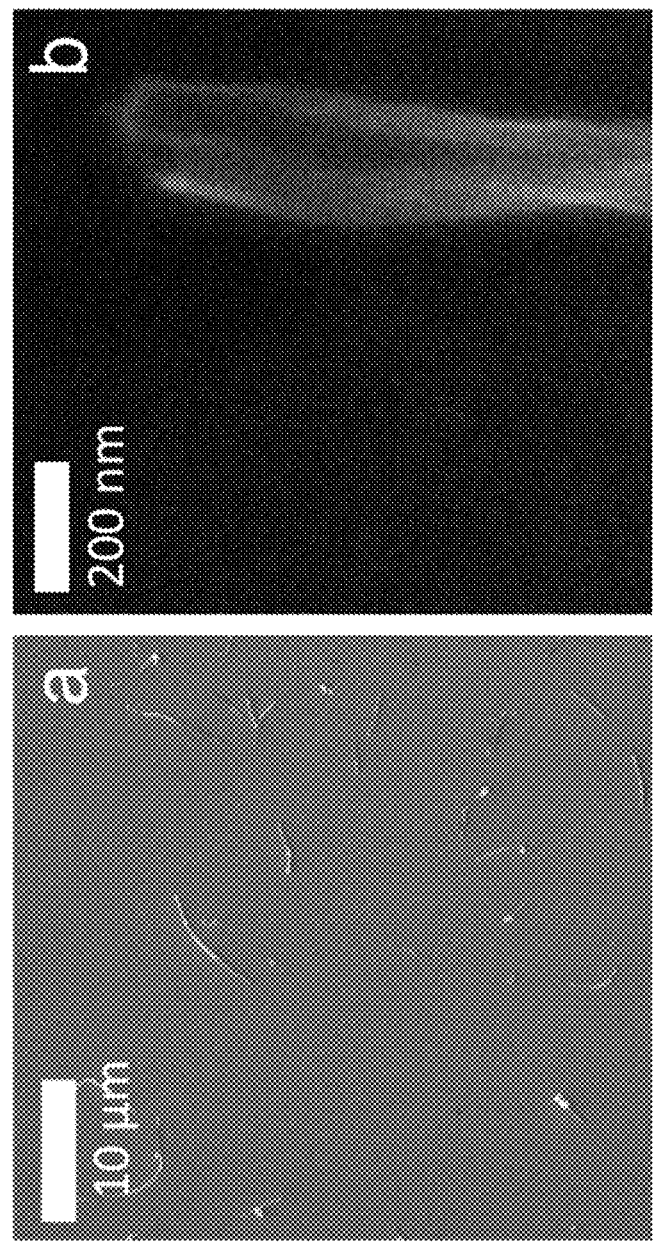
FIGS. 2A-2B are SEM images of PEG-GNRs.
Figures 2C, 2D:
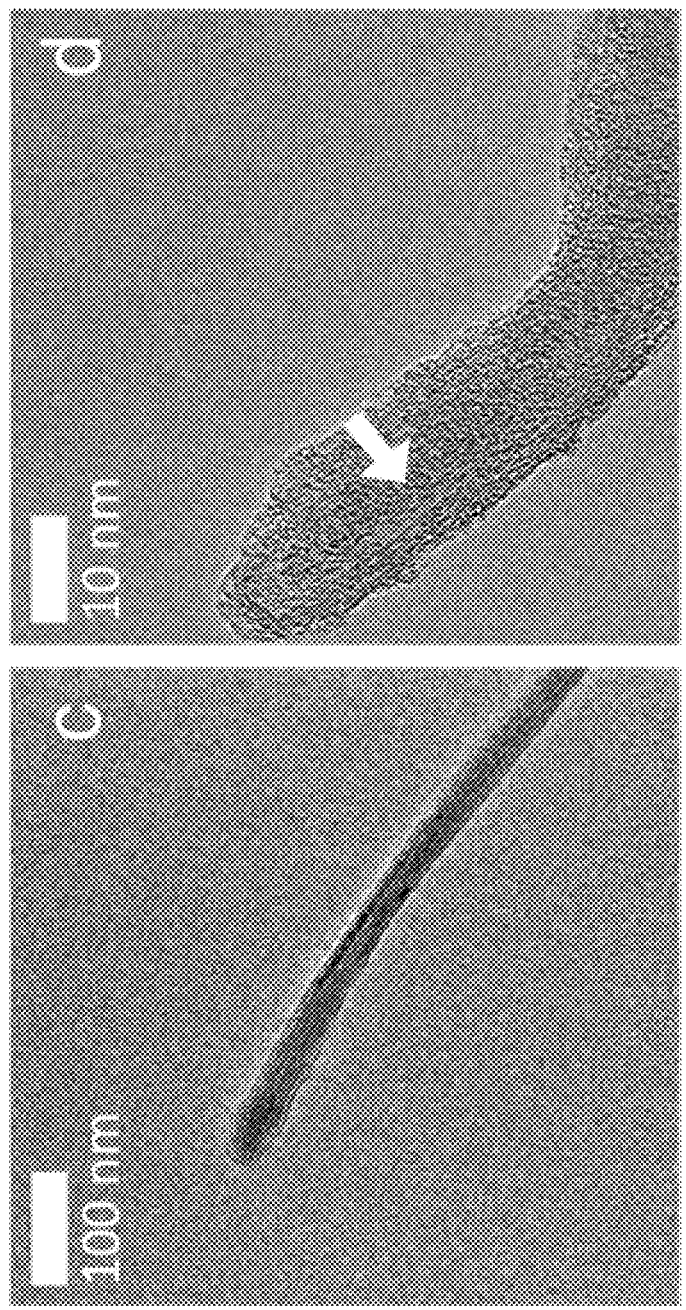
FIGS. 2C-2D are TEM images of PEG-GNRs.

For scanning electron microscope (SEM) analysis, the PEG-GNRs were dispersed in o-dichlorobenzene, briefly sonicated in a bath sonicator, and deposited on a smooth metal disk, from which the solvent was evaporated on a heat plate at <100° C. For transmission electron microscopy (TEM) analysis, the polyethylene glycol graphene nanoribbons (PEG-GNRs) were dispersed in water and drop cast onto a lacey carbon grid. The sample was imaged by an FEI Quanta 400 ESEM FEG instrument. FIGS. 2A-2B are SEM images of the PEG-GNRs. FIGS. 2C-2D are TEM images of the PEG-GNRs.

EXAMPLE 2

PEG-GNRs and Neuronal Fusogen Agent

The PEG-GNRs of Example 1 were dispersed in PEG600 (0.5 wt % by GNR concentration). The mixture was tightly sealed in a 50 mL conical vial and was sterilized by 120° C. pressurized steam for 30 min.

In embodiments of the present invention, the concentration of the PEG-GNRs is generally utilized at a low concentration (between 0.1 wt % and 5 wt %, and more generally between 0.5 wt % and 1 wt %).

Spinal Cord/Neuronal Treatment and Repair

In some embodiments, the present invention pertains to methods of facilitating neuronal treatment/repair in a subject by administering the compositions of the present invention to the subject. In some embodiments, the subject is a subject suffering from neuronal injury, such as spinal cord injury, brain damage, and the like. In some embodiments, the methods of the present disclosure can be utilized to facilitate neuronal healing in a subject that has undergone a treatment or a procedure, such as a whole-body transplantation surgery. In some embodiments, the treatment or procedure can be for treating other neurons in the nervous system or in the optical nerve.

The motor pathway is a group of neurons that connect the motor cortex of the brain to the motor neurons in muscle tissue which control muscle actuation. Damage to the spinal cord, or a complete severance of the spinal cord, prevents communication between muscle and brain, effectively paralyzing the individual.

Referring to FIGS. 3A-3F and FIGS. 4A-4F, these illustrate the natural repair (or lack thereof) of severance of, respectively, nerves in the peripheral nervous system (PNS) (motor neuron cell body 301 of the nerve cell and muscle tissue 302) and the central nervous system (CNS) (between CNS neuron cell bodies 401 and 402 of the nerve cells).

As shown in FIG. 3A, in the PNS, the nerve cell includes both a motor neuron cell body 301 and axon 303. The axon conducts electrical impulses between the motor neuron cell body 301 and the muscle tissue 302. As shown in FIG. 4A, in the CNS, one of the nerve cells includes CNS neuron cell body 401 and an axon 403. The other nerve cell includes CNS neuron cell body 402 and dendrite 404. The axons and dendrites provide the pathway from which electrical impulses are conducted.

Figures 3B, 4B:
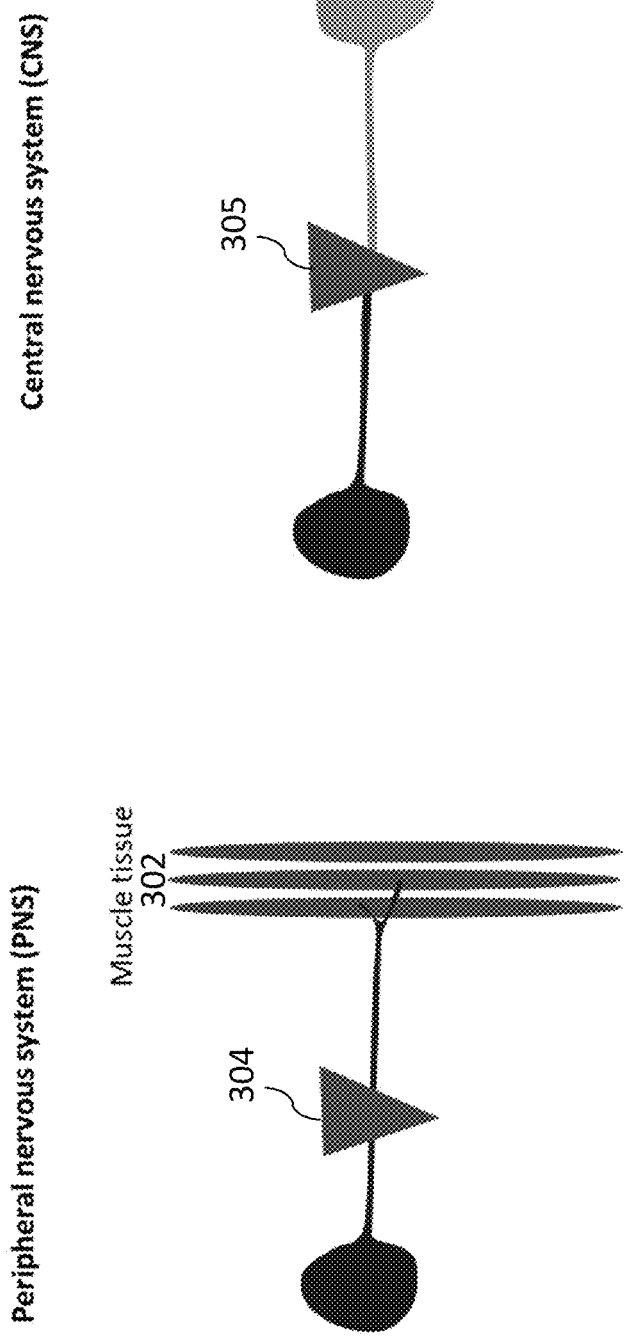

As shown in FIGS. 3B and 4B, a break or severance occurs (at severance 304 and 405, respectively).

Figures 3C, 4C:
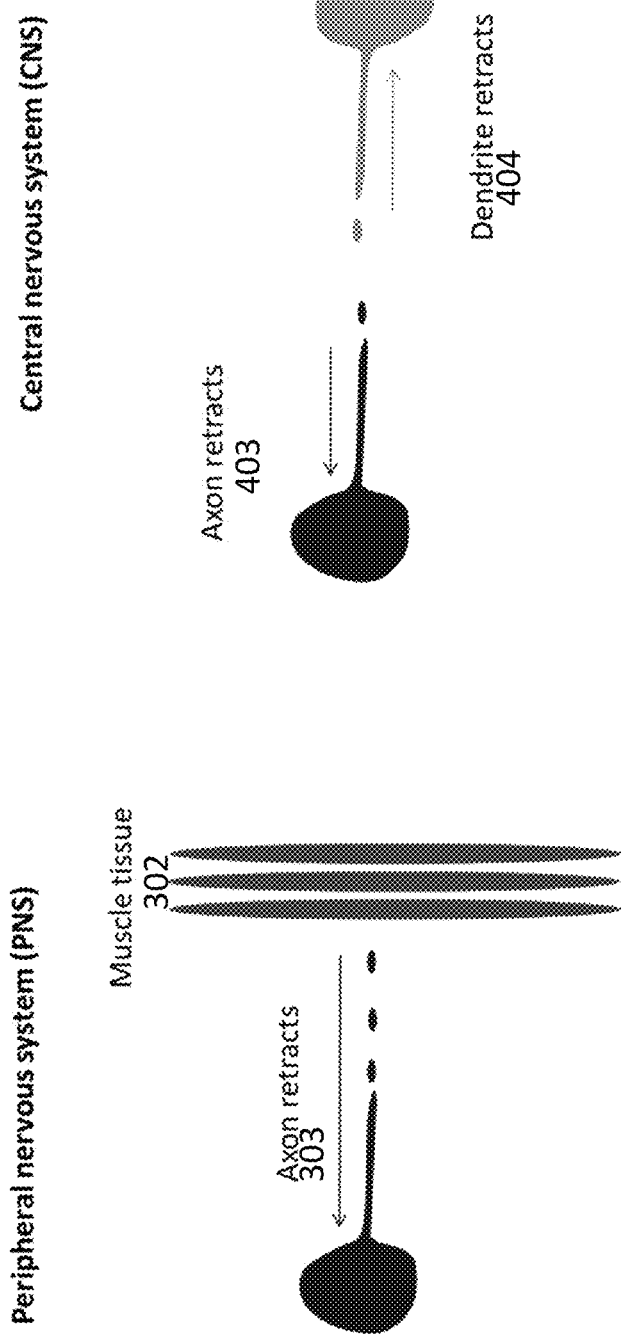

As shown in FIGS. 3C-3D, upon such break or severance, axon 303 retracts from muscle 302. As shown in FIGS. 4C-4D, upon such break or severance, axon 403 and dendrite 404 retracts from one another.

As shown in FIGS. 3E and 4E, axon 303, axon 403, and dendrite 404 experience regrowth.

Figures 3F, 4F:
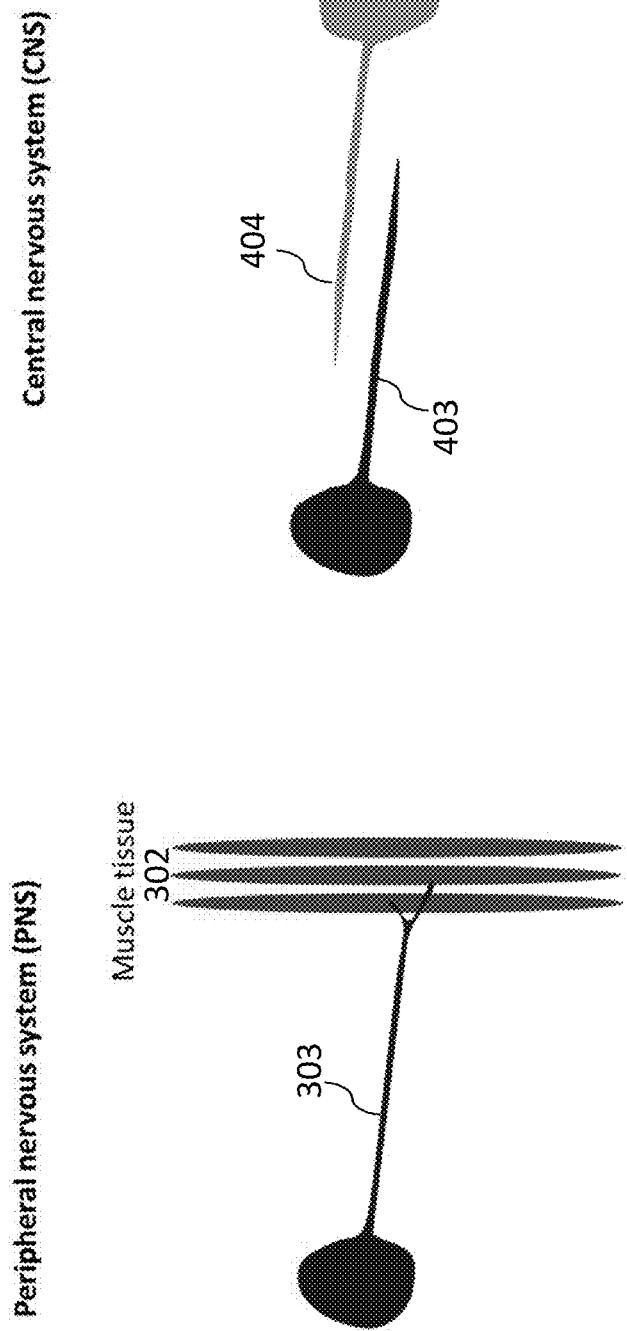
Figure 5:
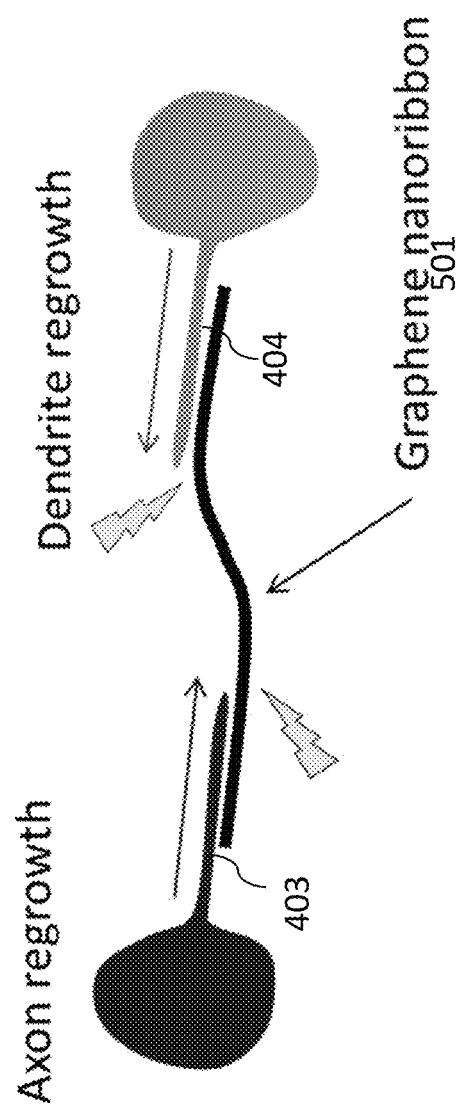
FIG. 5 illustrates a composition of the present invention being used as a neuronal scaffold to facilitate and re-establish the connection between the CNS neuron cell bodies.

For the PNS, the environment naturally encourages new growth and repair. Accordingly, as shown in FIG. 3F, axon 303 establishes a reconnection to muscle 302. However, for the CNS, the environment is hostile to new growth. Thus, connection between axon 403 and dendrite 404 is not re-established. As shown in FIG. 5, the composition (graphene nanoribbon 501) of the present invention can be used as a neuronal scaffold to facilitate the re-establishment between the CNS neuron cell bodies 401 and 402.

Figure 6:
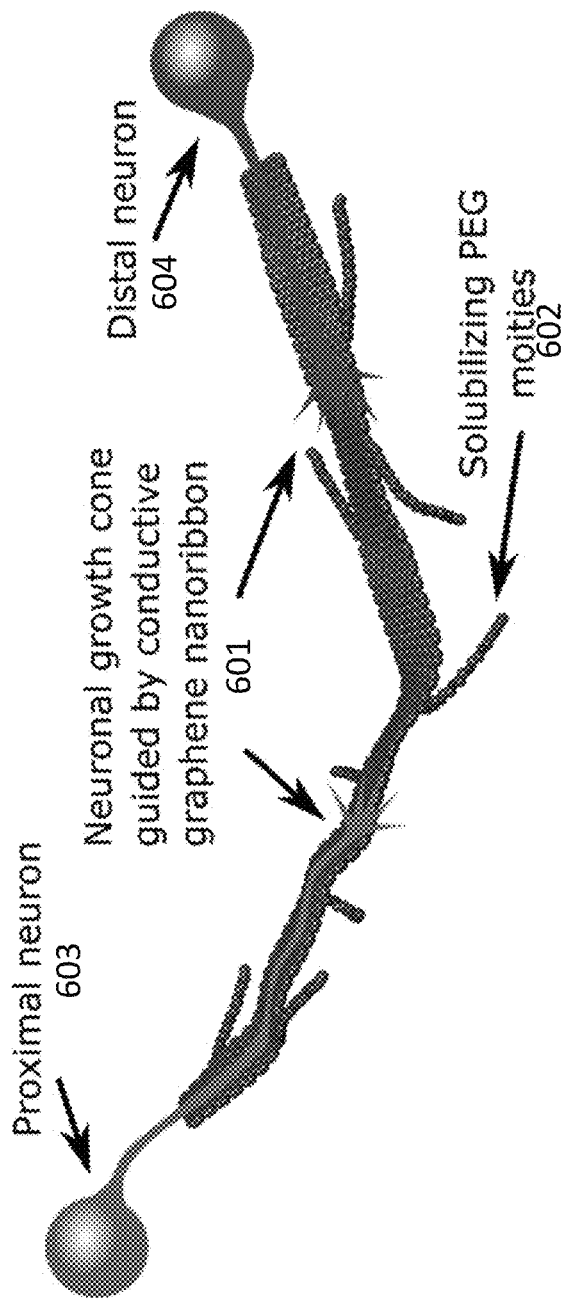
FIG. 6 illustrates a PEGylated GNR of the present invention that provides a neuronal growth code (guided by the conductive GNR) between the distal and proximal neurons.

FIG. 6 illustrates a PEGylated GNR (GNR 601 having solubilizing PEG moieties 602) that provides a neuronal growth code (guided by the conductive GNR 601) between the distal neuron 603 and the proximal neuron 604.

In some embodiments, the compositions of the present disclosure include a 1% solution of PEG-GNRs in PEG600. In such embodiments, it is believed that the PEG-GNRs act as a conductivity additive, as it has a concentration greater than the critical percolation threshold for these nanoribbons. It is further believed that the PEG600 acts as a fusogen agent, which serves to seal holes in neurons and fuse neurons across the gap.

In some embodiments, the synergy between the two components of the compositions of the present disclosure (e.g., PEG-GNRs and PEG600) allows each part of the mixture to act at different times. For instance, in some embodiments, the neuronal fusogen agent pulls the cut ends together over the first minute and fuses some (i.e., 1-5%) neurons together, which gives some structural support. This fusogen agent gets washed away rapidly (e.g., within 5 min-5 hours) Thereafter, the PEG-GNRs act as a conductive matrix to allow for action potentials to cross the gap (such as over the first 1-3 days). However, neurons grow along high aspect PEG-GNRs in the proper direction to provide anisotropic healing (i.e., isotropic healing prevents good connection, as the processes of the neurons are randomly directed, instead of directed towards the other cut end, as anisotropic healing provides).

In the past, large sheets of graphene or graphene oxide have been used in an attempt to allow for regrowth of spinal cord across an injury. In addition, there has been work with PEG, a fusogen, for spinal cords with scissions. While incremental progress has been made with both of these materials, various compositions of the present invention provide for a type of high aspect graphene that has not been used for spinal cord repair in conjunction with a neuronal fusogen (i.e., a combination that has never been used in the past).

Method of Treatment/Repair

Spinal cord repair is representative of the treatment and repair that can be performed with the present invention. However, the present invention is not limited to only spinal cord repair.

Figure 7:
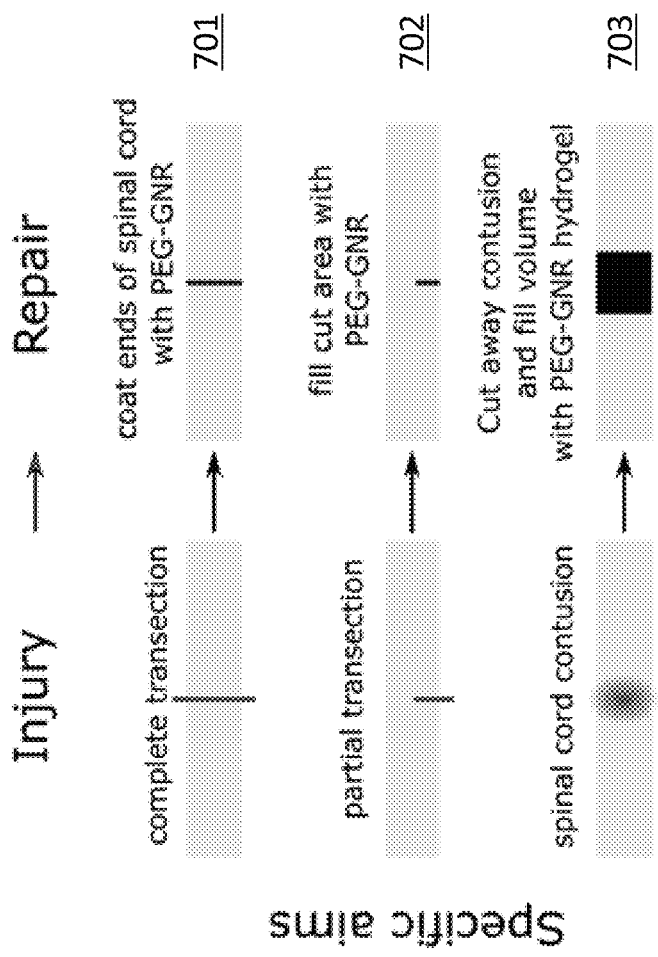
FIG. 7 illustrates different examples in which the present invention can be utilized for spinal cord repair.

The method of present invention is directed to using one of the above described compositions (such as PEG-GNRs and PEG600) and applying it to the area that needs to be repaired or treated. For instance, FIG. 7 illustrates different circumstances 701-703 in which the present invention can be utilized for spinal cord repair.

For circumstance 701, there is complete transection of the spinal cord. Water-soluble graphene having the fusogen agent (such as PEG-GNRs and PEG600) can be used to coat the ends of the spinal cord, and then the ends are contacted with one another. For circumstance 702, there is partial transection. The composition can be used by filling it in this cut area. For circumstance 703, there is spinal cord contusion. The contusion can be cut away or sliced into and the volume filled with the composition. Reducing inflammation of the area has shown some benefit, but potentially cutting out the bruised region and replacing it with a PEG-GNR hydrogel will allow the spinal cord to grow again. The hydrogel could even be seeded by neuronal stem cells isolated from the patient. A 3D graphene foams can also be used that can be oxidized above the edges and insert these into damages section. This will enhance the alignment of the GNR.

In methods of the present invention, shear can be used to align the PEG-GNR in the proper orientation. Shear will align the PEG-GNR due to the high aspect ratio of the GNR. In some embodiments, the PEG-GNR and PEG600 composition can be added, touch (or compress the area being treated), such as by touching the two ends of the severed spinal cord back together, and then slightly re-opening the gap for a moment, and then re-closing. This action will shear alignment and will cause the PEG-GNR to arrange longitudinally (which is the proper orientation).

Optionally, the cutting into or away of a small portion of the spinal cord can also be utilized in situations where there is a partial or complete severance of the spinal cord, or if there is a contusion. While the injured area may not be capable of being reconnected, by cutting a gap in the spinal cord (to expose previously unexposed portions), sites for union of the spinal cord can be created.

The PEG-GNRs thus act as highways for growth between top and bottom and bottom and top to have neurons collide and re-fuse. Plates would be larger diameter and less prone to direct the growth well since too wide for "highway directed" collision and re-fusion of the neurons.

Hence, the methods and compositions of the present invention provide at least three notable features. First, the high aspect ratio graphene nanoribbons provide a percolative conductivity path at a low concentration. Second, the synthetic route to these graphene nanoribbons means that they can be well-dispersed in aqueous solution, which is an important characteristic when dealing with biological systems. (If one had used plates of graphene the edge to basal plane ratio is slow low that the edge-addended sites concentration is so low that they are not well dispersed of solubilized. If one tries to functionalize on the basal planes, conductivity is lessened, and so they become less suitable for neuronal growth. Also, they cannot serve as the narrow highways for directing the neuronal reattachment.) Third, the synergy between a PEG-based fusogen and the GNRs allows for reliable and complete healing of the injury. Unlike graphene oxide, the edge functionalized GNRs are highly conductive, thereby serving as efficient platforms for neuronal re-growth and conduction through the spinal cord.

In some embodiments, the methods and compositions of the present invention reliably allow neuronal signals (e.g., motor evoked potentials (MEPs) and somatosensory evoked potential (SSEPs)) to cross the gap after 24 hours after complete transection of the spinal cord. (MEPs are recorded from muscles following direct stimulation of exposed motor cortex, or transcranial stimulation of motor cortex, either magnetic or electrical. SSEPs are used in neuromonitoring to assess the function of a patient's spinal cord during surgery; they are recorded by stimulating peripheral nerves, most commonly the tibial nerve, median nerve or ulnar nerve, typically with an electrical stimulus, which response is then recorded from the patient's scalp.)

In some embodiments, the compositions of the present invention can be utilized for almost perfect motor control recovery in rats and mice after 2 weeks. As such, various embodiments of the present disclosure represent a major advance over previous work, which gave only about 10% recovery of motor control after 4 weeks.

EXAMPLE 3

Surgery Using PEG-GNRs and Neuronal Fusogen Agent

To achieve a successful spinal cord fusion as required during cephalosomatic anastomosis (CSA), an effective technique to assure rapid re-innervation of the body across—primarily—the divided cervical spinal cord is necessary [Canavero 2013]. In the spinal cord fusion protocol called GEMINI, re-apposition of two sharply severed cords brings in contact the gray matter cores in which the cortico-truncoreticulo-propriospinal (CTRPS) pathway courses; this cellular core reestablishes contact by regrowth of the severed connections among propriospinal cells and by acute "fusion" of the neural membranes that were transected acutely. Concurrently, the integrity of a certain number of axons coursing in the long tracts of the white matter of the spinal cord will be restored [Canavero 2016].

It is this CTRPS pathway responsible for motor and coarse sensory transmission that is the linchpin of the GEMINI spinal cord fusion protocol [Canavero 2016]. In other words, PEG allows the process of spinal cord neural fusion in the long tracts of the white matter during the critical early stages of restoration of electrical continuity during spinal cord reconstruction. The effects differ substantially in the gray matter, where one would not expect axonal fusion as in the white matter, but rather a simple resealing (sealant effect of PEG) of the membranes of neurons injured by the nano-blade transection (akin to a neuroprotective effect).

The experiment of this example was carried out in accordance with animal ethics committee's guidelines and approved by the Institutional Animal Care and Use Committee of the Konkuk University. All procedures were performed in a manner that minimized suffering. Female Sprague-Dawley rats (250~280 g, Young Bio, Gyeonggi-do, Korea) were anesthetized using zoletil and xylazine (3:1 ratio, 1 ml/kg). The muscles overlying the cervical vertebral column were reflected exposing C4-6; a C5 laminectomy was performed and the dura mater split open longitudinally. After gently raising the cervical cord with a hook, full severance was performed with surgical sharp blades #11.

The experimental group (n=5) was treated with the PEG-GNR solution (0.5 mL per animal) directly applied at the level of transection of the cervical cord. The control group (n=5) was treated with the same volume of phosphate buffered saline. The muscle and fascia were sutured and the skin closed. Dextrose 5% solution (20 ml/kg) was administered daily via intraperitoneal injection.

EXAMPLE 4

Electrophysiology

Neuronal survival at the interface of the 2 apposed stumps is followed by re-sprouting and restoration of mechanical integrity. This process can be (and was) accelerated by electrical stimulation (electrophysiology). For neuron growth, sharp filamentous actin protrusions from the end of the growth cone of neurons can sense electrical and physical environment, which direct the tip of the neuron's growth process. See McCaig 2002.

One day after the surgery (of Example 3), the animals were re-anesthetized with urethane (1.25 g/kg, i.p.). Each animal was placed on a stereotaxic device (Narishige Scientific Instrument Laboratory, Tokyo, Japan) and artificially ventilated using a small animal respirator (Model 683, Rodent Ventilator, Harvard, Holliston, Mass., USA). Somatosensory evoked potentials (SSEPs) were recorded to measure the conduction recovery of the sensory system. A special electrode (NE-120, Rhodes Medical Instruments, Inc., Woodland Hills, Calif., USA) was used for SSEP recording. For the SSEP recording, the recording electrode was placed in the sensorimotor cortex (bregma: −2 mm, lateral: 2 mm; recording side). A bipolar platinum wire electrode placed in the contralateral sciatic nerve (stimulating side) was used as a stimulating electrode.

A single square pulse (0.1 ms duration) of electrical stimulus was delivered by a stimulus isolator (A365D, World Precision Instruments, Inc., New Haven, Conn., USA) that was driven by a pulse generator (Pulsemaster A300, World Precision Instruments). The analog signals of the evoked potentials were amplified (×10,000), filtered (Band-Pass 300-1,000 Hz), and fed to an IBM-compatible PC through an AD/DA converter (CED 1401, Cambridge, UK) to be averaged out using Spike 2 software. SSEP consisted of an average of 100-300 single sweep epochs. The effect of the stimulation intensity on SSEPs was analyzed in the wave forms by latencies and amplitudes.

Assessment

Modified Basso, Beattie, and Bresnahan (mBBB) scoring was employed to assess the rats following the above-described surgery and electrophysiology.

Figure 8:
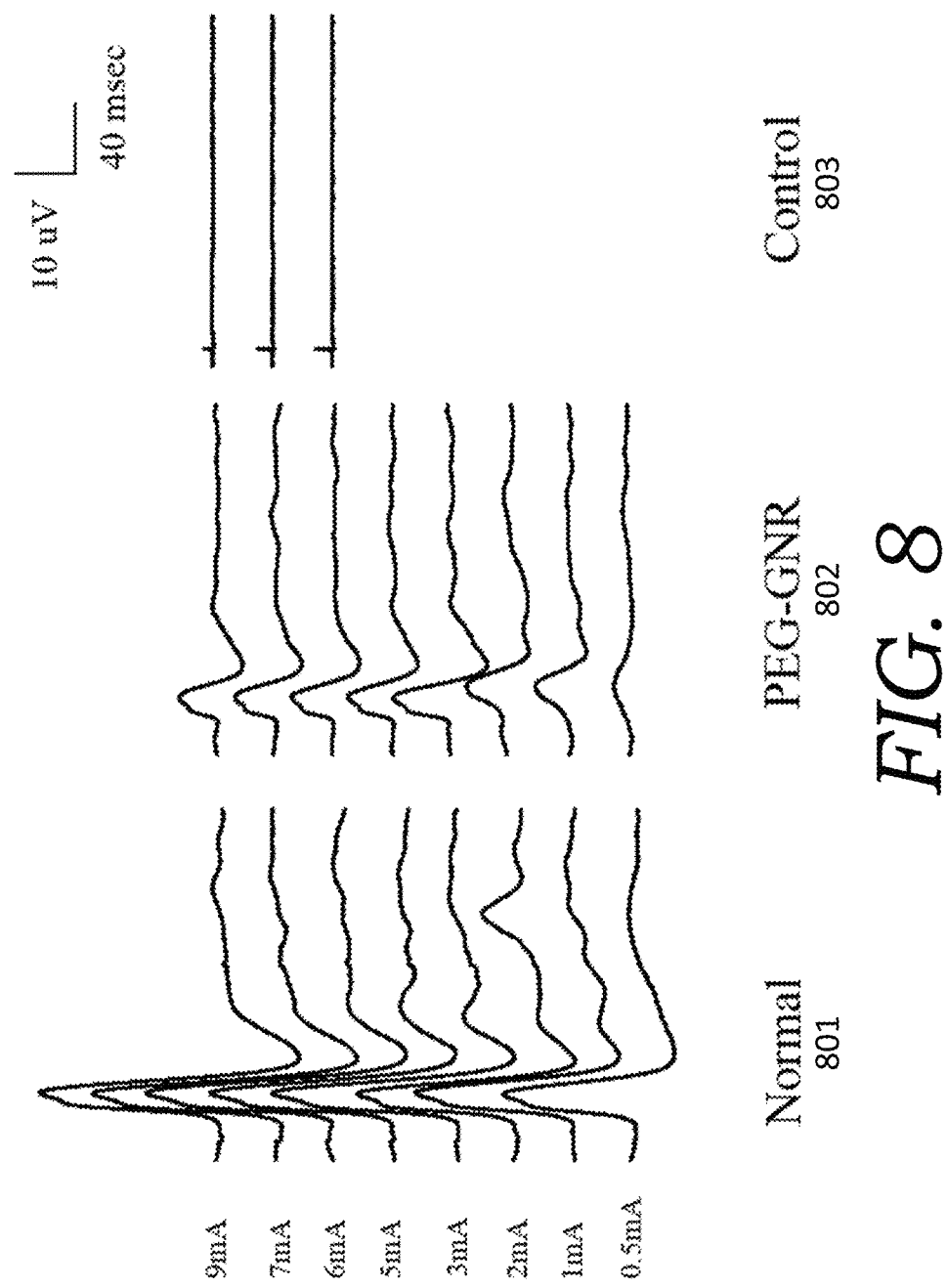
FIG. 8 are graphs of somatosensory evoked potential (SSEP) wave-forms for simulation of normal, PEG-GNR-treated (using an embodiment of the present invention), and control groups.

SSEPs were used to evaluate the functional integrity of ascending sensory pathways following surgery and topical treatment. SSEPs are a quantitative way to assess the conduction of somatosensory pathways following cervical cord transection. SSEPs were measured from normal rats (without transection) to acquire baseline recordings for comparison. See graph 801 of FIG. 8 The amplitude and latency parameters were classified as initial, N1- and P1-peak. Graphs 802-803 of FIG. 8 represent the amount of signal transduction through the site of severance and the speed at which the signal travels, respectively, for the PEG-GNR treated group and the control group. Graphs 802-803 are SSEP wave wave-forms by 6-mA stimulation in the experimental group 24 hrs after transection. As seen in graph 803, no SSEPs were detected in the control group. As seen in graph 802, the PEG-GNR-treated group exhibited SSEP recovery, although not yet at a normal level (after 24 hours).

Table 1 shows the in vivo electrophysiological analysis of the normal, PEG-GNR-treated, and control groups.

TABLE 1

In vivo Electrophysiology Analysis

| Groups | Latency (ms) | | | Amplitude (µV) | | |
| --- | --- | --- | --- | --- | --- | --- |
| | Initial | N1 | P1 | Initial | N1 | P1 |
| Normal | 9.70 ± 0.98 | 21.33 ± 3.39 | 39.87 ± 4.77 | 0.62 ± 0.36 | 58.28 ± 13.68 | 105.84 ± 32.72 |
| PEG-GNR | 9.70 ± 0.75 | 26.43 ± 2.22 | 49.33 ± 4.62 | 0.21 ± 0.05 | 6.03 ± 2.63 | 8.98 ± 3.75 |
| Control | — | — | — | — | — | — |

In Table 1, "N1" and "P1" are the first local maximum and local minimum of the recorded SSEP wave. "Initial" marks the point where the recorded SSEP wave starts. Latency measures the time between stimulation and recorded positions of the wave (with a lower time being better), and amplitude measures the intensity of the signal (with a higher amplitude being better).

Figure 9:
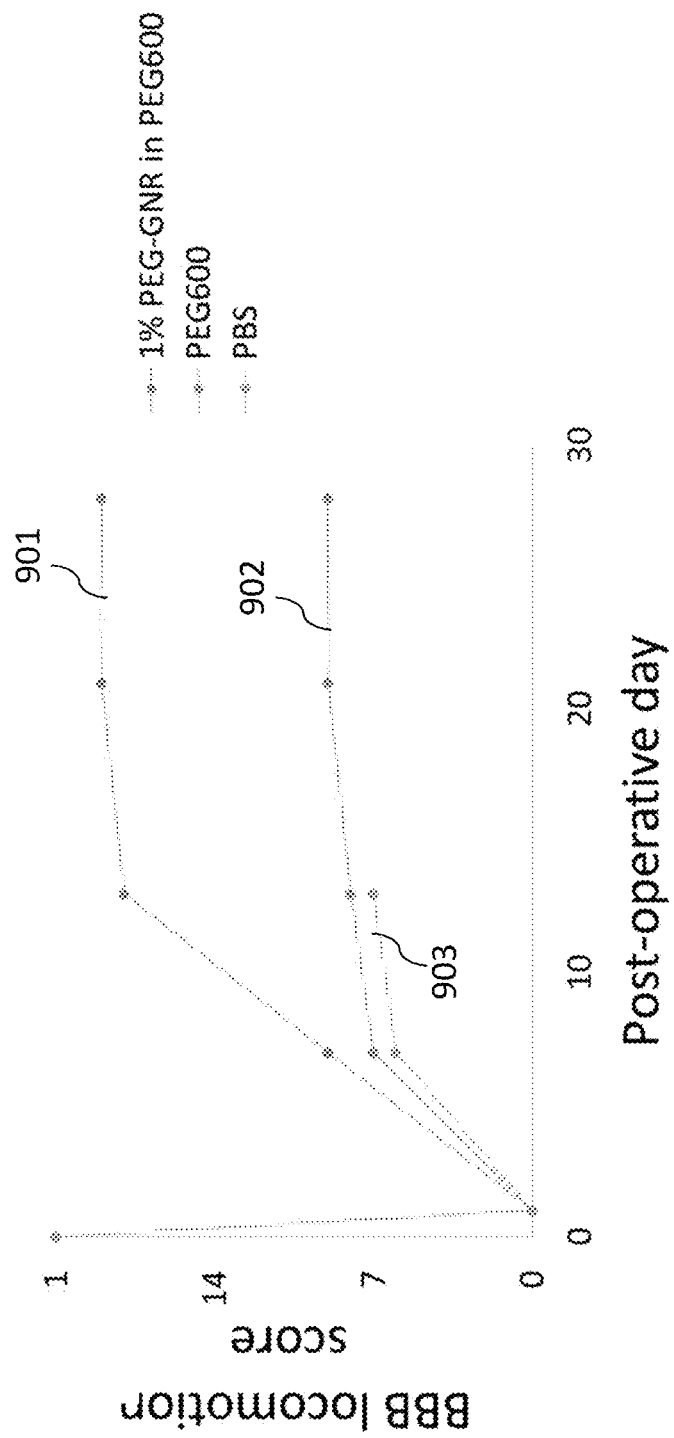
FIG. 9 shows the mobility recovery of one of the tested rats following intra-topical application of 1% PEG-GNR in PEG600 to blunt ends of transected spinal cord compared to PEG600 alone and PBS alone.

FIG. 9 shows the mobility recovery of the tested rats following intra-topical application of 1% PEG-GNR in PEG600 (plot 901) to blunt ends of transected spinal cord compared to PEG600 alone (plot 902) and PBS alone (plot 903). As shown in plot 901, recovery in the rats was steady. This was significantly better as compared to PEG600 alone and PBS alone, which plateaued at 8 and 7, respectively.

Furthermore, for the first rat tested, 24 hours after surgery weak tremors of the forelimbs were apparent. Two days later, slight voluntary movements of all 4 paws were occasionally present (mBBB score of fore limbs & hind limbs: 4, 4 respectively). At 1 week, active movements were clearly evident, but balance was not possible (mBBB score of fore limbs & hind limbs: 8, 9 respectively). Two weeks later, the rat could walk—although not completely normally—without losing balance, stand up on his hind limbs and use his forelimbs to feed himself with pellets (mBBB score of fore limbs & hind limbs: 18, 19 respectively).

For the rats tested, somatosensory evoked potentials (SSEP) were restored to ~30% of their pre-surgery amplitude within 24 hours after complete cervical transection and application of 0.5 mL of a 1% PEG-GNRs solution in PEG600. Two weeks after the surgery, an additional animal (that did not have their SSEPs measured) recovered to score 19 out of 21 on the BBB motility scale through this simple intra-topical administration at the lesion site in the transaction.

These examples show how the conductive graphene nanoribbon additive to PEG [N. Kim 2016; Lu 2013] affords a quick recovery of neurophysiologic sensory transmission in the spinal cord. The behavioral recovery in the rat was unexpected and quite remarkable.

As made clear elsewhere [Canavero II 2015], the faster the sensorimotor recovery in the injured patient, the fewer complications from prolonged immobilization.

Animal studies have shown that restitution of membrane continuity takes many minutes of absolute immobility of the axon segments in the presence of PEG and even more time for the repair to become permanent [Canavero I 2015; Canavero II 2015; Canavero 2013]. This can be achieved by stabilizing the point of transection with a negative pressure micro-connector within which PEG is circulated [Canavero 2016]: this allows immediate delivery of the selected fusogen combined with a stable mechanical apposition for extended time until mechanical stability is achieved. For the present invention, in order to mimic the gentle apposition afforded by this connector, PEG-GNRs were infused into the gap left by the sharp transection at C5 in which the 2 stumps of the spinal cord of rats were kept in mechanical proximity by simple hyperextension of the head. The result has great benefit.

Applicants have recently shown how a sharp transection aided by PEG alone can restore at least partial motor function in rats and mice [C. Kim I 2016; C. Kim II 2016] and neurophysiologic transmission [Ye 2016]. This is the first time that the effects of a locally applied water-soluble, PEGylated conductive graphene nanoribbon solution on neurophysiologic conduction after sharp cervical cord transection in rats have been reported. Evidence suggests that molecular weights of PEG of <1000 Daltons may be toxic in humans [Canavero 2013]. PEG-GNRs have no apparent potential to trigger acute or chronic toxicity. No side effects have been observed to date. Thus, Applicants report for the first time on the effect of a novel form of PEG with the goal of rapid reconstruction of a sharply severed spinal cord.

It is believe that this fusion of transected axons was made possible by exploiting fusogens, such as polyethylene glycol (PEG), i.e., substances that restore the integrity of acutely transected nerve fibers both in peripheral nerves and sharply transected spinal cords. Despite PEG' s properties having been discovered in 1986, very little work has been published over the past 30 years [Canavero 2013; Ye 2016]. Acute transections in humans being rare, no group pursued a clinical application of this technology. A head-body transplant and the need for an accelerated spinal cord fusion protocol resurrected these older studies. Actually, fusogens exert their beneficial effect maximally when applied locally to the point of transection rather than when administered parenterally [Ye 2016].

In a 3D tissue setting, across a gap in the spinal cord, Applicants believe the graphene nanoribbons to first act as an electrical conduit, and then act as an electrically active scaffold upon which the neurons will grow, directing their processes in the proper direction across the gap. Applicants believe this because GNR that have been patterned on 2D surfaces cause growing and differentiating neurons to take on the same pattern. See Akhavan 2013. Only a very small concentration of PEG-GNRs in the fusogen was required because at <1 wt % of high aspect ratio rod-like carbon nanostructures in polymers, electrical percolation can be achieved.

Advantages

Spinal cord treatment/repair has the potential to reduce the cost of care for such injuries while improving outcomes and potentially reversing paralysis. Spinal cord repair is a solution to most, if not all, problems associated with spinal cord injuries (SCI) resulting from acute injuries, including contusions and cuts. The resulting symptoms associated with SCI largely draw their cause from the inability of the brain to communicate with the lower body and internal organs, causing limb and organ dysfunction. If the spinal cord could be repaired, a large percentage of the symptoms of SCI could be ameliorated. However, recovery from spinal cord injury (SCI) requires the successful regeneration of both long- and short-segment axons across an injury site to permit the re-establishment of severed connections. For effective regeneration, the nerve cells must overcome major obstacles: (1) physical barriers to growth such as the post-injury glial scar, and (2) chemical barriers to growth as numerous hostile biological substances are released as a result of the injury. The establishment a permissive growth environment is crucial for such regeneration.

Methods utilizing the present invention have shown that graphene nanoribbons (GNRs) are able to overcome the natural phenomena that prevent spinal cord recovery following SCI. These chemically modified GNRs have been shown to stimulate neuronal growth on their surfaces, and to be nontoxic. These provide a microenvironment that is conducive to neuronal growth and a scaffold that can electropositionally inform the growth cones of neuronal processes.

Treatment with GNRs goes far beyond the normal treating of inflammation in damaged spinal cords or other secondary problems associated with SCI which do not treat the root cause—they are temporary measures that only stave off the inevitable decline in health and early death associated with SCI. Although many candidate drugs have shown great promise as neuroprotective agents when examined using in vitro assays for spinal cord repair, only a few have realized their potential when applied using in vivo models of CNS trauma. One main reason for this failure is their inability to cross the blood-brain barrier.

The present invention provides an electrically conductive nano-scaffold that may be surgically implanted via laminectomy or at the time of spinal column stabilization, and at the same time may be doped with neurotrophic and neuroprotective factors and neural stem cells. An externally applied (transcutaneous) electrical field (portable device worn by the patient) may then help to stimulate and direct axonal growth. The scaffold can be crosslinked by various polymers, including polymers that would allow for the nanoribbons to self-align and crosslink once injected into the spinal cord area.

Utility

The methods and compositions of the present invention can be utilized for various applications. In addition to healing patients who have spinal cord injury or completely severed spinal cords, the compositions of the present disclosure could be used to restore neuronal connection in people who have been paralyzed for less than 30 years.

In some embodiments, the compositions of the present disclosure could facilitate (e.g., be the final key to) the solving of the problem of whole body transplants, which will allow the transplant of a healthy head (e.g., the head of a person with muscular dystrophy, or the head of a person suffering some gross damage to their body, or the head of a person whose body is failing due to age or disease) onto a donor body (e.g., the body of a brain dead individual).

The PEG-GNRs of the present invention can also be used for peripheral nerve repair after injury, brain interconnect repair after tumor extraction and bits of the brain were lost in the process, and this can extend to areas where brain had been damaged due to accident or gun shot, for example re-growing neurons through application of a drop of the PEG-GNR in PEG600 to the damaged area in the brain.

The present invention can also be used for address chronic muscle and nerve pain from dystrophic firing in the spinal cord, prevent infection associated with feeding and breathing tubes, help alleviate depression by giving patients hope of returning to a more normal life, and restore autonomic control of lower internal organs, like the bladder and bowel.

Furthermore, in some embodiments, the compositions of the present invention can also include an antioxidant. The antioxidant can be used, for example, to reduce the oxidative stress of the initial injury and surgery, and also provide antioxidants systemically to mitigate superoxide-induced damage and swelling. The anti-oxidants can include, for example, PEG-functionalized hydrophilic carbon clusters (PEG-HCCs), PEG-functionalized graphene quantum dots (PEG-GQDs), PEG-polycyclic compounds (e.g., perylene diimide derivatives), and combinations thereof. In some embodiments, the compositions of the present disclosure include less than 1 wt % of GNRs.

While embodiments of the invention have been shown and described, modifications thereof can be made by one skilled in the art without departing from the spirit and teachings of the invention. The embodiments described and the examples provided herein are exemplary only, and are not intended to be limiting. Many variations and modifications of the invention disclosed herein are possible and are within the scope of the invention. Accordingly, other embodiments are within the scope of the following claims. The scope of protection is not limited by the description set out above.

The disclosures of all patents, patent applications, and publications cited herein are hereby incorporated herein by reference in their entirety, to the extent that they provide exemplary, procedural, or other details supplementary to those set forth herein.

Concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a numerical range of approximately 1 to approximately 4.5 should be interpreted to include not only the explicitly recited limits of 1 to approximately 4.5, but also to include individual numerals such as 2, 3, 4, and sub-ranges such as 1 to 3, 2 to 4, etc. The same principle applies to ranges reciting only one numerical value, such as "less than approximately 4.5," which should be interpreted to include all of the above-recited values and ranges. Further, such an interpretation should apply regardless of the breadth of the range or the characteristic being described.

Unless defined otherwise, all technical and scientific terms used herein have the same meaning as commonly understood to one of ordinary skill in the art to which the presently disclosed subject matter belongs. Although any methods, devices, and materials similar or equivalent to those described herein can be used in the practice or testing of the presently disclosed subject matter, representative methods, devices, and materials are now described.

Following long-standing patent law convention, the terms "a" and "an" mean "one or more" when used in this application, including the claims.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that can vary depending upon the desired properties sought to be obtained by the presently disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, the term "and/or" when used in the context of a listing of entities, refers to the entities being present singly or in combination. Thus, for example, the phrase "A, B, C, and/or D" includes A, B, C, and D individually, but also includes any and all combinations and subcombinations of A, B, C, and D.

REFERENCES

Tour J. M. et al., Solvent-Based Methods For Production of Graphene Nanoribbons, PCT Int'l Patent Publ. No. WO 2013/040356, filed Sep. 14, 2012 ("Tour PCT '356 Application").

Tour J. M. et al., Graphene Nanoribbons Prepared From Carbon Nanotubes Via Alkali Metal Exposure, PCT Int'l Patent Publ. No. WO 2010/147860, filed Jun. 11, 2010 ("Tour PCT '860 Application").

Tour J. M. et al., Three-Dimensional (3D) Printing Of Graphene Materials, PCT Int'l Patent. Appl. No. PCT/US17/41768, filed Jul. 12, 2017 ("Tour PCT '768 Application").

Akhavan, O. et al., Differentiation Of Human Neural Stem Cells Into Neural Networks On Graphene Nanogrids. *J. Mater. Chem. B* 2013 1:6291-6301 ("Akhavan 2013").

Canavero S. et al., Neurologic foundations of spinal cord fusion (GEMINI). *Surgery* 2016 160(1):11-19 ("Canavero 2016").

Canavero S., Commentary. *Surg Neurol Int* 2015 6:103 ("Canavero I2015").

Canavero S., The "Gemini" spinal cord fusion protocol: Reloaded." *Surg Neurol Int* 2015 6:18 ("Canavero II 2015").

Canavero S., HEAVEN: The head anastomosis venture Project outline for the first human head transplantation with spinal linkage (GEMINI). *Surg Neurol Int* 2013 4(Suppl 1):S335-342 ("Canavero 2013").

Genorio, B. et al., In Situ Intercalation Replacement and Selective Functionalization of Graphene Nanoribbon Stacks. *ACS Nano* 2012, 6, 4231-4240 ("Genorio 2012").

Kim C. Y., PEG-assisted reconstruction of the cervical spinal cord in rats: effects on motor conduction at 1 h. *Spinal Cord* 2016 54, 910-912 ("C. Kim I2016").

Kim C. Y. et al., Gemini: Initial Behavioral Results After Full Severance Of The Cervical Spinal Cord In Mice. *Surg Neurol Int.* 2016 Sep. 13; 7(Suppl 24):S629-31 ("C. Kim II 2016").

Kim N. D. et al., Microwave Heating of Functionalized Graphene Nanoribbons in Thermoset Polymers for Wellbore Reinforcement. *ACS Applied Materials & Interfaces* 2016 8(20): 12985-12991 ("N. Kim 2016").

Kosynkin, D. V. et al., Highly Conductive Graphene Nanoribbons by Longitudinal Splitting of Carbon Nanotubes Using Potassium Vapor. *ACS Nano* 2011, 5, 968-974 ("Kosynkin 2011").

Kosynkin, D. V. et al., Longitudinal Unzipping of Carbon Nanotubes to Form Graphene Nanoribbons. *Nature* 2009, 458, 872-826 ("Kosynkin 2009").

Leipzig N. D. et al., Differentiation of neural stem cells in three-dimensional growth factor-immobilized chitosan hydrogel scaffolds. *Biomaterials* 2011 32(1):57-64 ("Leipzig 2011").

Lu W. et al., Functionalized graphene nanoribbons via anionic polymerization initiated by alkali metal-intercalated carbon nanotubes. *ACS Nano* 2013 7(3):2669-2675 ("Lu 2013").

McCaig C. D. et al., Has Electrical Growth Cone Guidance Found Its Potential. *Trends Neurosci* 2002 25(7):354-359 ("McCaig 2002").

Palejwala, A. H. et al., Biocompatibility of Reduced Graphene Oxide Nanoscaffolds Following Acute Spinal Cord Injury in Rats. *Surg. Neurol. Int.* 2016, 7, 75 ("Palejwala 2016").

Sinitskii, A. et al., Electronic Transport in Monolayer Graphene Nanoribbons Produced by Chemical Unzipping of Carbon Nanotubes. *App. Phys. Lett.* 2009, 95, 253108-1-3 ("Sinitskii 2009").

Ye Y. et al., Fusogen-assisted rapid reconstitution of anatomophysiologic continuity of the transected spinal cord. *Surgery* 2016 160(1):20-25 ("Ye 2016").

What is claimed is:

1. A composition comprising
   (a) functionalized graphene nanoribbons, wherein
      (i) the functionalized graphene nanoribbons comprise water solubilizing addends functionalized at the edges of the graphene nanoribbons, and
      (ii) the functionalized graphene nanoribbons are soluble or dispersible in water; and
   (b) a fusogen agent, wherein
      (i) the fusogen agent is in a liquid form,
      (ii) the functionalized graphene nanoribbons are soluble or dispersible in the fusogen agent, and
      (iii) the composition is a solution of the functionalized graphene nanoribbons in the fusogen agent.

2. The composition of claim 1, wherein the functionalized graphene nanoribbons are water soluble.

3. The composition of claim 1, wherein the functionalized graphene nanoribbons in the composition is in an amount between about 0.1 wt % and about 5 wt %.

4. The composition of claim 1, wherein the amount of the functionalized graphene nanoribbons in the composition is between about 0.5 wt % and about 1 wt %.

5. The composition of claim 1, wherein the fusogen agent is hydrophilic.

6. The composition of claim 1, wherein the composition is capable for use as a fusogen in a method selected from the group consisting of spinal cord repairs, spinal cord treatments, neuronal repairs, neuronal treatments, brain tissue repairs, brain tissue treatments, and whole-body transplants.

7. The composition of claim 1, wherein the addends comprise polyethylene glycol (PEG).

8. The composition of claim 1, wherein the addends are selected from the group consisting of polyethylene glycol (PEG), ethylene oxide, propylene oxide, vinyl acetate, vinyl monomers, water soluble electrophiles, polypropylene glycol, polyethylene imine (PEI), PEG-PEI block copolymers, polyvinyl pyrrolidone (PVP), polyvinyl alcohol (PVA), polyacrylic acid, dextrose, starch, pectin, agarose, polysaccharides, 2-aminoethanesulfonic acid, and combinations thereof.

9. The composition of claim 8, wherein the fusogen agent is hydrophilic, and the functionalized graphene nanoribbons are soluble or dispersible in the fusogen agent.

10. The composition of claim 1, wherein the fusogen agent comprises polyethylene glycol (PEG) having an average molecular weight greater than 500 grams per mole.

11. The composition of claim 1, where the fusogen agent comprises polyethylene glycol (PEG) having an average molecular weight of 600 grams per mole (PEG600).

12. The composition of claim 1, wherein the fusogen agent is selected from the group consisting of polyethylene glycol (PEG), poly(vinyl alcohol), poly(acrylic acid), poly(hydroxyalkyl acrylates), poly(hydroxalkyl methacrylates), and combinations thereof.

13. The composition of claim 1, wherein the functionalized graphene nanoribbons have an electrical conductivity of at least about 0.1 S/cm.

14. The composition of claim 13, wherein the electrical conductivity is at least about 1 S/cm.

15. The composition of claim 14, wherein the electrical conductivity is at least about 10 S/cm.

16. The composition of claim 1, wherein the functionalized graphene nanoribbons have an electrical conductivity that is at least 10% of electrical conductivity of pristine graphene nanoribbons.

17. The composition of claim 1, wherein
    (a) the composition comprises a 3D graphene scaffold, and
    (b) the 3D graphene scaffold is a support of the functionalized graphene nanoribbons.

18. The composition of claim 1, wherein
    (a) the functionalized graphene nanoribbons further comprise the addends functionalized on the basal planes of the graphene nanoribbons, and
    (b) at least 90% of the addends functionalized on the graphene nanoribbons are functionalized on the edges of the graphene nanoribbons.

* * * * *